(12) United States Patent
Gould et al.

(10) Patent No.: US 8,951,784 B2
(45) Date of Patent: Feb. 10, 2015

(54) CELL CULTURE BIOREACTOR

(75) Inventors: Dennis Richard Gould, Half Moon Bay, CA (US); Hrair Kirakossian, San Jose, CA (US)

(73) Assignee: Sepragen Corporation, Hayward, CA (US)

( * ) Notice: Subject to any disclaimer, the term of this patent is extended or adjusted under 35 U.S.C. 154(b) by 1887 days.

(21) Appl. No.: 11/638,992

(22) Filed: Dec. 13, 2006

(65) Prior Publication Data

US 2007/0134790 A1    Jun. 14, 2007

Related U.S. Application Data

(60) Provisional application No. 60/750,219, filed on Dec. 14, 2005.

(51) Int. Cl.
*C12M 1/00* (2006.01)
*C12N 5/07* (2010.01)
*C12N 5/02* (2006.01)
*C12M 1/12* (2006.01)
*C12M 3/00* (2006.01)
*C12N 5/071* (2010.01)

(52) U.S. Cl.
CPC .............. *C12M 23/40* (2013.01); *C12M 25/14* (2013.01); *C12M 29/10* (2013.01)
USPC ..................... 435/289.1; 435/325; 435/299.2; 435/304.1; 435/366

(58) Field of Classification Search
None
See application file for complete search history.

(56) References Cited

U.S. PATENT DOCUMENTS

| | | | |
|---|---|---|---|
| 4,833,083 A | | 5/1989 | Saxena |
| 4,840,730 A | | 6/1989 | Saxena |
| 4,865,729 A | | 9/1989 | Saxena et al. |
| 4,889,812 A | * | 12/1989 | Guinn et al. ............... 435/286.7 |
| 5,041,216 A | | 8/1991 | Henzler et al. |
| 5,057,428 A | | 10/1991 | Mizutani et al. |
| 5,073,491 A | * | 12/1991 | Familletti ..................... 435/382 |
| 5,187,095 A | | 2/1993 | Bliem et al. |
| 5,256,298 A | | 10/1993 | Powell |
| 5,376,548 A | | 12/1994 | Matsuo et al. |
| 5,462,659 A | | 10/1995 | Saxena et al. |
| 5,976,870 A | * | 11/1999 | Park .......................... 435/286.5 |
| 6,844,187 B1 | | 1/2005 | Wechsler et al. |
| 6,979,308 B1 | | 12/2005 | MacDonald et al. |
| 7,033,823 B2 | | 4/2006 | Chang |
| 7,163,825 B2 | | 1/2007 | Gault |
| 2004/0058434 A1 | | 3/2004 | Gault |

* cited by examiner

*Primary Examiner* — Jon P Weber
*Assistant Examiner* — Aaron J Kosar
(74) *Attorney, Agent, or Firm* — Rutan & Tucker, LLP

(57) ABSTRACT

A cell culture bioreactor having a culture chamber for cell growth, a culture medium reservoir mounted externally to the culture chamber, a fluid circulation mechanism for moving culture medium from the reservoir through the culture chamber, and an aerating mechanism for introducing air into and removing air from the culture chamber is provided. The cell culture bioreactor comprises a manifold mechanism mounted at the top end of the culture chamber, a fluid circulation mechanism fluidly connected to the culture medium reservoir, for receiving culture medium from the culture medium reservoir and distributing culture medium into the culture chamber. A support matrix is mounted within the culture chamber in fluid communication with the fluid circulation mechanism with at least a portion of the support matrix contacting the culture medium wherein the culture medium flows from the manifold means in a thin film over substantially the entire surface of the support matrix allowing the biological cells to grow on the support matrix.

15 Claims, 5 Drawing Sheets

AWSM Bioreactor

CELL CULTURE BIOREACTOR

The present application claims benefit of priority of provisional patent application Ser. No. 60/750,219, filed by Dennis R. Gould and Hriar Kirakossian, on Dec. 14, 2006, titled "Cell Culture Bioreactor".

FIELD OF THE INVENTION

The present invention relates generally to cell culture and more specifically to a novel bioreactor for growing cells for culture and harvesting.

BACKGROUND OF THE INVENTION

Pharmacologically significant biological products for research and therapy are manufactured largely using various cell culture technologies (Chu et al., "Current Opinion in Biotechnology" (2201) 12: 180-187). Monoclonal antibodies, recombinant proteins/peptides including vaccines, produced by such technologies, are currently on the market or in active, phased development world wide. World wide demand for large scale cell culture production, therefore, continues to increase.

Currently, the industry standard method for large scale cell culture is suspension-perfusion technology. Prior art devices and methods disclose interrupted exposure to oxygenation by continually and alternately the dipping of cells in out of culture media or moving cells in and out of submersion by a moving belt. These methods and devices compromise between minimizing shear stress on the cells and oxygenation. A few examples of current methods used for cell culture are described briefly below.

U.S. Pat. No. 5,256,298 issued Oct. 26, 1993 to Paul E. Powell, discloses an device and method which use a continuous, moving belt of resilient, open-cell foam polymer to establish a turbulent flow of fluids. The belt moves alternately bulk liquid and gas phases to enable mass transfer polymer surface and the liquid and/or gas as a consequence of compression and release of the belt.

United States Patent No. 20040058434 issued Mar. 25, 2004 to Philippe Gault, describes a reactor for cell and tissue culture which involves mechanical stimulation of tissues or cells and supply of nutrients by way of a culture medium suitable for structural tissues. An optimum levels of nutrient and oxygen supply necessary for growth of cells or tissues, is achieved by reducing the density of cells and the preparation of implants in a variety of forms, compositions and applications.

U.S. Pat. No. 7,033,823 issued Apr. 25, 2006, to King-Ming titled "Chang Cell-cultivating device" teaches a cell culture method and device where a growth substrate capable of providing a large surface area for cell adhesion. By intermittently and periodically providing sufficient oxygen and nutrients to the cells without causing cell death, it also functions also as an oxygenator, a depth filter and a static mixer to maximize the production of cellular products. The optimum levels of oxygenation and nutrient are regulated by controlling the amount of culture medium that comes into contact with the growth substrate means.

United States Patent Application No. filed Mar. 25, 2005, by Code Kind and Philippe Gault, titled "Bioreactor For Tissue Cultivated In The Form Of a Thin Layer and Uses Thereof" teaches cell culture methods that grow cells on a thin film held between two plates. This method is specifically designed for tissue implants, but not for the growth of cells by direct exposure to liquid/air interface.

All these methods suffer from major disadvantages in that they have to continuously compromise between sufficient movement of culture media across cell membranes to provide them nutrients for sufficient growth and, at the same time provide sufficient $O_2/CO_2$ gas exchange rates, without limiting rate of movement of these elements, to minimize shear-stress to the cells. This is a serious dilemma, and currently "dealt with" by reducing cell density to levels that are supported by the limited gas exchange rates. They are not suitable for large scale production as they are not directly scalable.

It would be highly desirable to have a bioreactor device and method available that provides maximal oxygen transfer to all cells in the culture in a substantially equivalent manner while, at the same time, supplies sufficient nutrients for cell growth in high density, convenient product harvesting and ready scalability.

It is thus an object of the present invention to provide a high performance and high density bioreactor for cell growth and culture.

It is another object of this invention to provide a method and device for cell culture where the cells are continuously, rather than intermittently, bathed in a culture medium with zero shear-stress, while simultaneously and continuously supplied essential nutrients and exposed to optimal $O_2/CO_2$ gas exchange.

It is an object of the present invention to provide a novel bioreactor for the culture of cells without having to immerse the cells in the growth medium.

Another object of the present invention is to provide a bioreactor for cell culture wherein the cells are continuously and simultaneously fed and aerated to achieve maximum growth in a relatively short time.

Yet another object of the present invention is to provide a bioreactor which is directly scalable to workable proportions.

Yet another object to provide an "accelerated wicking" process for the distribution of the growth medium across the surface of cell support matrix.

Additional objects, advantages and novel features of the invention will be set forth in part in the description and drawings which follow, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed broadly to a high performance bioreactor for cell culture The present invention provides a high performance bioreactor device and method for culturing biological cells on a support matrix. The bioreactor device of the present invention uses support matrices comprising a porous material having continuous open pores that permit the substantially free transport of liquids and gases through the support matrix. The bioreactor device of the present invention uses a gravity-assisted capillary or wicking process to evenly distribute a thin layer or film of the nutrient rich, culture medium, across the surface of the porous support matrix where the cells of interest are immobilized. The device also provides for the simultaneous oxygenation of the cells by flowing air across the surface of and through the porous support matrix.

In one embodiment of the present invention, biological cells are immobilized on the surface of the support matrix with a thin film of culture medium continuously flowing over its surface. In another embodiment, the support matrix is formed of interlacing and interconnected fibers of a material compatible with the biological cells being cultured. Another important feature of the invention is the regulation of the flow of culture medium over the support matrix ensuring the maintenance of a thin film of medium over substantially the entire surface of the support matrix. In yet another aspect, such regulation is accomplished by monitoring the back pressure of the air or other gas or gases, such as $O_2$ or $CO_2$, introduced into the culture chamber of the invention.

The bioreactor device of the present invention comprises the following elements: (a) a culture chamber having an inlet, an outlet, and an interior; (b) a support matrix with a top end and a bottom end, mounted in the interior of the culture chamber for holding biological cells on the support matrix, the support matrix comprising a porous material having continuous open pores, such material being formed of interlacing and interconnected fibers and having a non toxic surface suitable as a substrate for biological cells; the continuous open pores of such material permitting substantially equivalent communication with the interior of the culture chamber from any location on the surface of the support matrix; (c) a first reservoir mounted outside the bioreactor for holding a culture medium; (d) a second reservoir for the culture medium supported at the top end of the reservoir directly above the top end of the support matrix; (e) fluid circulation means having a fluid delivery rate for non-turbulently delivering culture medium to the support matrix, such that the culture medium flows in a thin film over substantially the entire surface of the support matrix to the bottom end of the support matrix and the chamber which is then removed or recycled through the outlet; and (f) circulation means for supplying oxygen or other gas or gases, as are suitable for growth of the cells, to the surface of the support matrix and through the support matrix to the interior of the culture chamber.

In another embodiment of the present invention, the support matrix divides the interior of the culture chamber into a first region and at least one second region. The device further comprises a gas inlet in communication with the first region and a gas outlet in communication with the at least one second region, the gas inlet and gas outlet being operationally connected to a regulated source of air for the culture chamber that provides a flow of air from the gas inlet through the support matrix to the gas outlet. Preferably, the first region of the culture chamber has a first pressure and the at least one second region of the culture chamber has a second pressure, such that the first pressure is substantially equivalent to the second pressure, i.e. there is no back pressure due to the culture medium impeding the flow of air through the support matrix.

In another aspect, the bioreactor device of the present invention further comprises a regeneration means operationally associated with the fluid circulation means, the regeneration means (a) receiving the culture medium from the outlet, (b) optionally removing waste material or extracting product from such culture medium, (c) optionally replenishing nutrients to such culture medium, and (d) delivering the culture medium to the fluid circulation means.

In yet another embodiment, the present invention provides a method for high performance cell culture comprising the following steps: (a) providing a culture chamber having an inlet, an outlet, an interior, and a support matrix mounted in the interior for holding biological cells, the support matrix comprising a porous material having continuous open pores, such material being formed of interlacing and interconnected fibers or porous foam, and having a non toxic surface suitable as a substrate for biological cells, the continuous open pores of such material permitting substantially equivalent communication with the interior of the culture chamber from any location on the surface of the support matrix; (b) introducing a culture medium containing biological cells into the culture chamber and allowing the biological cells to become immobilized on the support matrix; and (c) non-turbulently delivering a flow of culture medium to the support matrix, such that (1) the flow of culture medium travels in a thin film over substantially the entire surface of the support matrix to a reservoir at the bottom end of the support matrix and through the outlet, (2) substantially none of the continuous open pores of the support matrix are flooded by the flow of culture medium, (3) circulating fluid reaches the bottom of the support matrix, turbulent free, thus preventing foam formation, and (4) simultaneously flowing a stream of air gently across and through the surface of the support matrix such that there is no back pressure generated by the flow of the medium across the surface of the matrix.

DETAILED DESCRIPTION OF THE INVENTION

Figure 1:
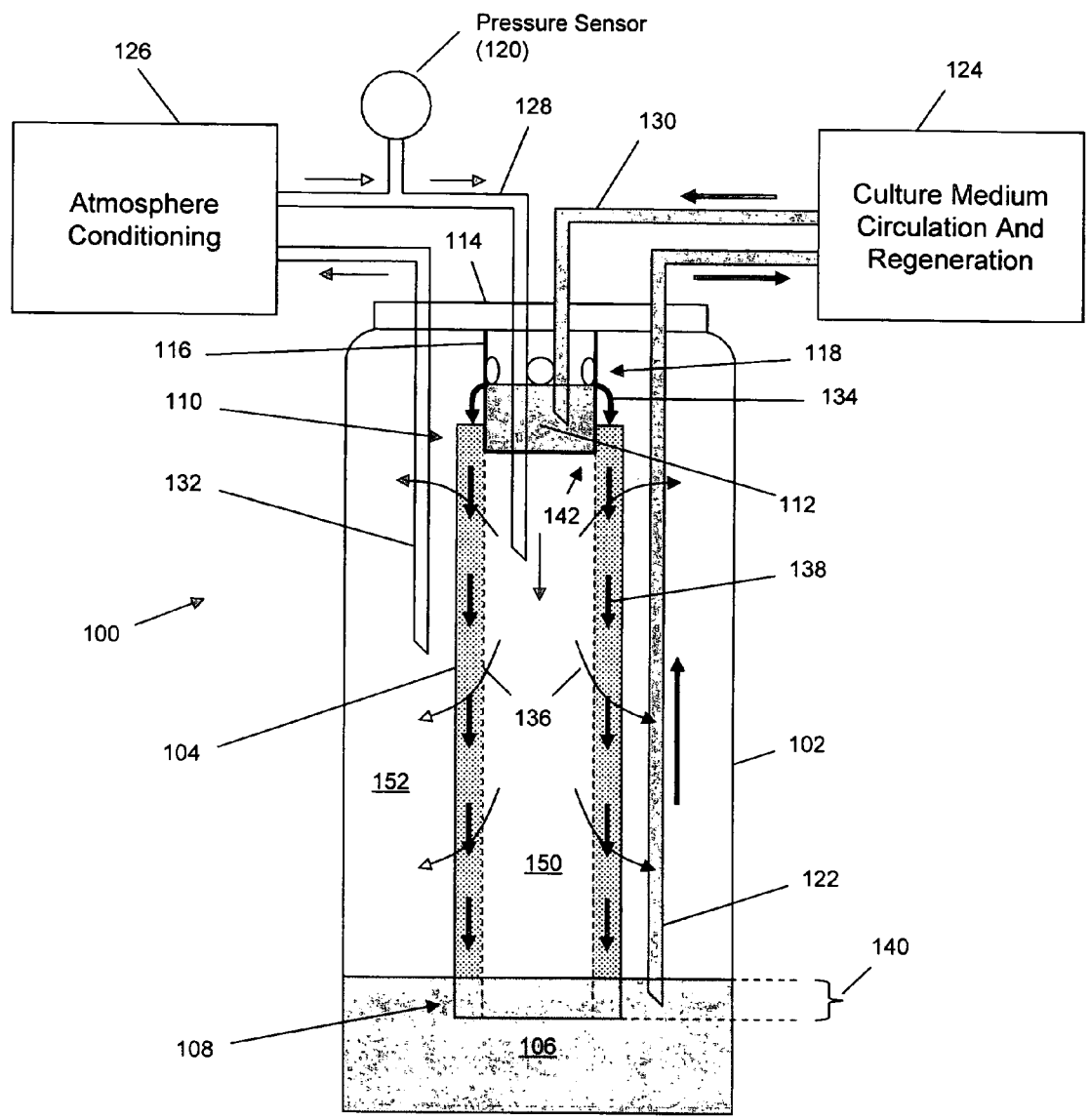
FIG. 1 is a side view illustrating a cell culture bioreactor, constructed in accordance with the present invention.

The invention provides a method, system, and device for supporting large-scale continuous, or batch culturing of biological cells, by culturing cells directly on the support matrix. In an alternative mode, the invention also provides a method and device for continuously aerating, and in particular oxygenating a culture medium used to support a bioreactor by acting as a gas exchanger (a "lung") only, with no cells immobilized on the support matrix. In this aspect cells are NOT grown directly on the "lung", but are grown, in a conventional bioreactor (i.e. hollow fiber or suspension culture), partitioned from the support matrix. The support matrix oxygenates the culture fluid, but cells are grown in a connected (but partitioned) conventional bioreactor.

A novel feature of the invention is the simultaneous and continuous oxygenation and nourishment of the biological cells being cultured. This is achieved by the use of a support matrix that is a porous material having continuous open pores for simultaneously aerating biological cells and at the same time supplying nutrients for their growth and sustenance. The material for the support matrix is formed of interlacing and interconnected fibers, or porous foam, that are non toxic to cells but with a surface suitable for a culture medium to flow over it in a thin layer or film, such that even the continuous flow of a thin layer of culture medium, air flow through the material will be substantially unrestricted. Typically, a thin layer or film of the growth or culture medium has a thickness of from a few µm, e.g. 1 µm, to about 1 mm, i.e. 100 µm. As used herein, the term "thickness" in reference to a thin film or layer of culture medium means the perpendicular distance from the surface of the support matrix to the liquid-air interface of the culture medium. "Substantially unrestricted" in reference to air flow through a support matrix of the invention means that the presence of a flow of the culture medium over the surface of such support matrix does not impede the passage of air through the pore system of the support matrix. Such substantially unrestricted flow of air or any other gas conducive to the growth of the cells of interest, through a support matrix of the invention is important to ensure that every location on the support matrix is substantially equivalent with respect to the exchange of air or gases between the culture medium and the ambient atmosphere. The unimpeded flow of gas through a support matrix in an embodiment of the device of this invention depends on several factors including, but not limited to, the flow rate of the culture medium through the support matrix, the viscosity of the culture medium, the surface tension forces between the culture medium and the support matrix surface, the flow rate of the air, the detailed structure of the support matrix, and the like.

The bioreactor of the present invention comprises a three dimensional culture chamber, cylindrical, rectangular or any other shape capable of easy handling. It may be constructed of glass, or any other chemically non-reactive, bio-compatible material like ceramic, stainless steel and the like. A support matrix comprising a three-dimensional porous sponge or reticulated foam or wicking filter or other materials used in humidifiers, is mounted at the top of the chamber directly above the support matrix. A non-turbulent recirculation/distribution system is second reservoir for the culture medium is mounted directly above the support matrix. A first reservoir for holding the culture medium is mounted either at the base of the culture chamber and/or connected to an exterior reservoir. A second reservoir for holding the culture medium is mounted at the top of the support matrix. The culture medium from the first reservoir is pumped into the second reservoir through tubing whose delivery end is submerged in the liquid contained in the second reservoir to eliminate surface splashing turbulence. The second reservoir is designed to allow even distribution of over-flow which then flows directly onto the top of the support or wicking matrix, again avoiding air/fluid splashing turbulence. This turbulence free medium distributor allows very rapid, non-turbulent delivery of culture medium to the top of the wicking matrix.

The fluid delivered to the top of the support or wicking matrix flows evenly and uniformly down the matrix by gravity-assisted capillary/wicking flow and collects at the bottom of the chamber. An outlet for removal or recycling of the spent medium is provided near the bottom of the culture chamber. The spent medium is then pumped back to the first reservoir for recycling or is discarded. The bottom or lower end of the matrix is positioned to just touch or slightly submerge in the spent culture medium flowing down the support matrix. This turbulence free circulation of the medium through the entire system, substantially eliminates undesirable and denaturing foaming and other effects.

Support matrices suitable for use in the device of this invention may be synthetic or natural porous, three-dimensional matrices. Pore sizes may vary from from 10 µm to 100 µm or more to allow the capture, entrapment and/or binding of the cultured cells up to ten or more millimeters to allow free, unobstructed gas exchange throughout the matrix even while the culture medium is flowing through it. Such materials must also be capable of sterilization and stable over a long period of use. They must also be chemically modifiable for certain types of cell growth. They must all be stable over a long period of use. Pore size of the matrix must be large enough to support high density cell growth and still allow free flow of air throughout the matrix. The support matrix chosen must be such that the flow of fluid across its surface is achieved by any or a combination of gravity assisted capillary/wicking and gravitational forces as defined herein, rather than by direct pumping pressure required in gas permeable membrane systems, which generates fluid turbulence. Materials for the support matrix must also have adequate capillary and adsorption characteristics ("wicking") to allow a rapid, thin film of fluid to traverse the fibrous structures of the matrix. Suitable materials include but are not limited to natural vegetable sponge, more specifically "loopha" sponge, or animal sponges. Synthetic sponges made from polyurethane or other synthetic materials which meet the above criteria may be utilized. Other hydrophilic, hydrophobic charged or neutral matrices are also suitable for use as the support matrix, depending on the nature and properties of the cells of interest. Preferred materials include celluose based expanded "Wicking Filter" such as those used in humidifiers to maximize air/wicking liquid surface areas, macroporous poly (DL-lactide) foams, loofa sponge, three-dimensional polyvinyl-alcohol matrices and the like.

The growth or culture medium is distributed across and through the support matrix in a continuous, rapidly flowing, thin fluid film can bathe the cultured cells (growing in the pathway of the fluid flow) thereby maintaining an open pathway, throughout the support matrix to allow for a continuous gas exchange. The three-dimensional porous structures present a large liquid/air surface and minimize saturation or flooding.

Examples of cell types for culture and harvesting, using the bioreactor of this invention include but are not limited to monoclonal antibody secreting hybridoma cells derived from mice, rats, rabbit or human, Eukaryotic cells, biochemical markers, recombinant peptides or nucleotide sequences of interest, proteins, yeast, insect cells, stable or viral infected, avian cells or mammalian cells such as CHO cells, monkey cells, lytic products and the like for medical, research or commercial purposes.

Culture media normally used for tissue culture are suitable for use as a culture medium in the bioreactor of this invention. Examples include but are not limited to DMEM or RPMI formulations known in the art, with or without fetal bovine serum, penicillin, L-glutamine, streptomycin and other culture additives in common use. Other nutrients used for specific situations and which promote the growth of particular cells of interest may also be incorporated into the culture medium.

A typical embodiment of the device of this invention is illustrated in FIG. 1. The device 100 comprises (i) a culture chamber 102 with a lid 114, (ii) a support matrix 104 in the form of a hollow cylinder having an interior 150, a top end 110, a bottom end 108, and being mounted inside the chamber 102 with the top end 110 sealably attached to a manifold 116 so that whenever reservoir 106 of culture medium is present, the interior 150 communicates with the region 152 only through pores of the support matrix 104, (iii) an inlet 130 for introducing culture medium and/or biological cells to the support matrix 104, (iv) an outlet 122 for removing culture medium from the chamber 102 for regeneration or removal of waste products and/or desired products, (v) fluid circulation means 124 for driving the culture medium through the culture chamber 102, and (vi) air or gas conditioning means 126 for driving air or other gases into the chamber 102 for circulation through support matrix 104. Culture medium from the inlet 130 is delivered to manifold 116 that non-turbulently distributes culture medium to the top end 110 of the support matrix 104.

The uniform non-turbulent distribution of the culture medium to the top end 110 of the support matrix 104 can be accomplished in many different ways and is a matter of design choice of one of ordinary skill in the art. As illustrated in FIG. 1, manifold 116 is a receptacle that receives the culture medium 112 which then flows through multiple ports 118 spaced around the manifold 116 so that culture medium flows 134 through such ports onto the top surface of the support matrix 104. A number of ports are selected so that the flow of the culture medium is evenly, or uniformly, distributed to the top surface of the support matrix 104. Receptacle 112 optionally may not be provided with ports 118 for flow of culture medium but by over flow of the culture medium after it fills the receptacle. The culture medium then flows, for example by gravity, and capillary forces, from the top end 110 of the support matrix 104, through the support matrix 104 as illustrated by arrows 138, to the bottom end 108 of the support matrix 104, and into the reservoir 106. This non-turbulent flow prevents the formation of foam, a serious problem seen with many conventional systems.

From the reservoir 106, the culture medium is then driven, or siphoned, out of the chamber 102 through the outlet 122. The support matrix 104 extends into the reservoir 106 only enough to maintain a fluid connection between the bottom surface of support matrix 104, preventing foam causing turbulence, and reservoir 106; thus, distance 140 is close to zero, preferably, at most 1-2 mm.

In one aspect, a conditioned atmosphere optimized for the objectives of the culture (e.g. growth rate, product synthesis, etc.) is flowed into the first interior region 150 of the culture chamber 102 through a gas inlet 128. Preferably, pressure sensor 120 is operationally connected to the gas inlet 128 so that any back pressure or resistance to a steady gas flow can be detected. From the first interior region 150, atmosphere flows 136 through the pores of the support matrix 104 into the second interior region 152 of the culture chamber 102, after which it is removed via an exhaust port 132, which may be a simple, sterile filtered vent, or other conventional means to maintain a conventional sterile exhaust system, preventing microbial contamination from back-flowing into the bioreactor sterile field, may carry the atmosphere to an atmosphere conditioning station where it is prepared for recycling.

Figure 4:
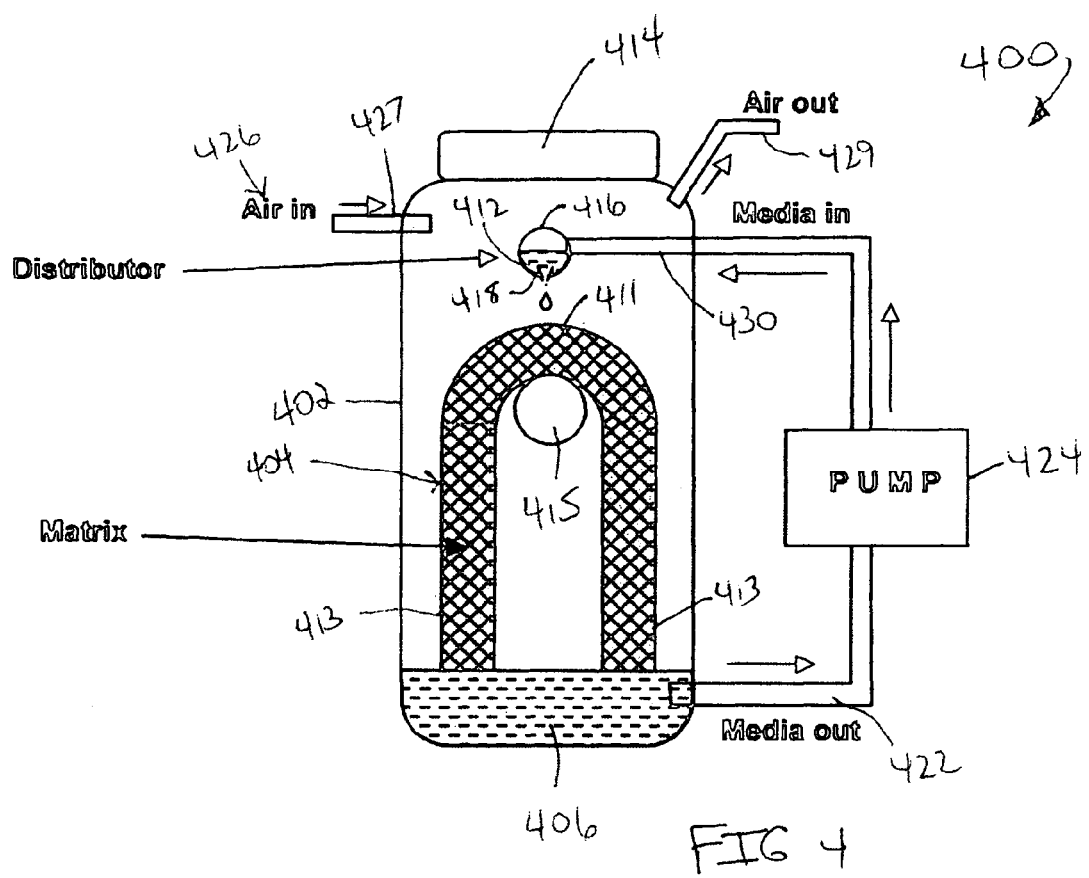
FIG. 4 is a perspective view illustrating another embodiment of a cell culture bioreactor, constructed in accordance with the present invention.
Figure 5:
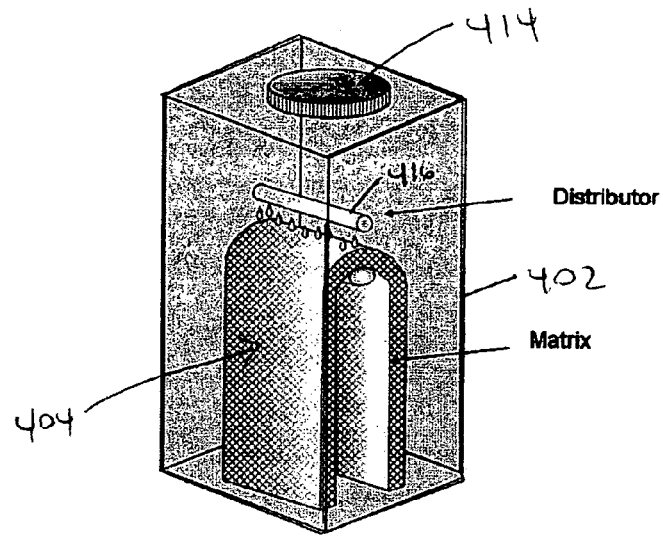
FIG. 5 is a another perspective view illustrating the cell culture bioreactor of FIG. 4, constructed in accordance with the present invention.
Figure 6:
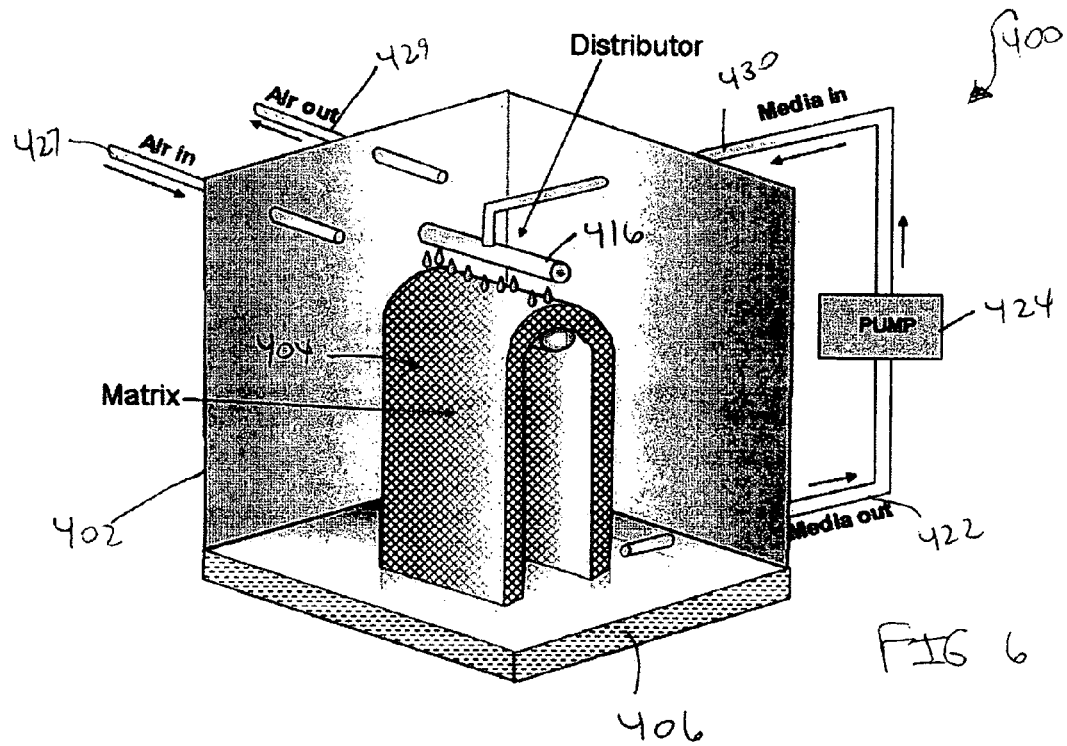
FIG. 6 is a sectional view illustrating the cell culture bioreactor of FIG. 4, constructed in accordance with the present invention.

Another embodiment of the invention is illustrated in FIGS. 4-6. Device 400 comprises (i) a culture chamber 402 with a lid 414, (ii) a support matrix 404 in the form of a sheet having a middle portion 411, ends 413, and being mounted inside the chamber 402 with the middle portion 411 draped over a support rod 415, (iii) a manifold 416 positioned above the middle portion 411 and the support rod 415 so that whenever reservoir 406 of culture medium is present, (iv) inlet 430 for introducing culture medium and/or biological cells through the manifold 416 to the support matrix 404, (v) outlet 422 for removing culture medium from the chamber 402 for regeneration or removal of waste products and/or desired products, (vi) fluid circulation means 424 for driving the culture medium through the culture chamber 402, and (vii) atmosphere conditioning means 426 having an air inlet 427 and an air outlet 429 for driving atmosphere into the chamber 402 for circulation through the support matrix 104. The culture medium from the inlet 430 is delivered to the manifold 416 that non-turbulently distributes culture medium to the middle portion 411 of the support matrix 404.

The uniform non-turbulent distribution of culture medium to the middle portion 411 of the support matrix 404 can be accomplished in many different ways and is a matter of design choice of one of ordinary skill in the art. As illustrated in FIGS. 4-6, the manifold 416 is a receptacle that receives culture medium 412 which then flows through multiple ports 418 spaced along the manifold 416 so that culture medium flows through such ports onto the middle portion 411 of the support matrix 404. A number of ports are provided so that the flow of culture medium is evenly, or uniformly, distributed to the middle portion 411 of the support matrix 404. The culture medium then flows, for example by gravity, and capillary forces, from the middle portion 411 of the support matrix 404, through the support matrix 404 as illustrated by the arrows 438, to the ends 413 of the support matrix 404, and into the reservoir 406. This non-turbulent flow prevents the formation of foam, a serious problem seen with many conventional systems.

From the reservoir 406, the culture medium is then driven, or siphoned, out of the chamber 402 through the outlet 422. The ends 413 of the support matrix 404 extend into the reservoir 406 only enough to maintain a fluid connection between the bottom surface of the support matrix 404, preventing foam causing turbulence, and the reservoir 406.

With this embodiment, similar to the first embodiment, a conditioned atmosphere optimized for the objectives of the culture (e.g. growth rate, product synthesis, etc.) is flowed into the culture chamber 402 through the air inlet 427. Preferably, a pressure sensor (not shown) is operationally connected to the air inlet 427 so that any back pressure or resistance to a steady gas flow can be detected. The atmosphere flows through the pores of the support matrix 404 after which it is removed via the exhaust port 429, which may be a simple, sterile filtered vent, or other conventional means to maintain a conventional sterile exhaust system, preventing microbial contamination from back-flowing into the bioreactor sterile field, may carry the atmosphere to an atmosphere conditioning station where it is prepared for recycling.

Figure 2A:
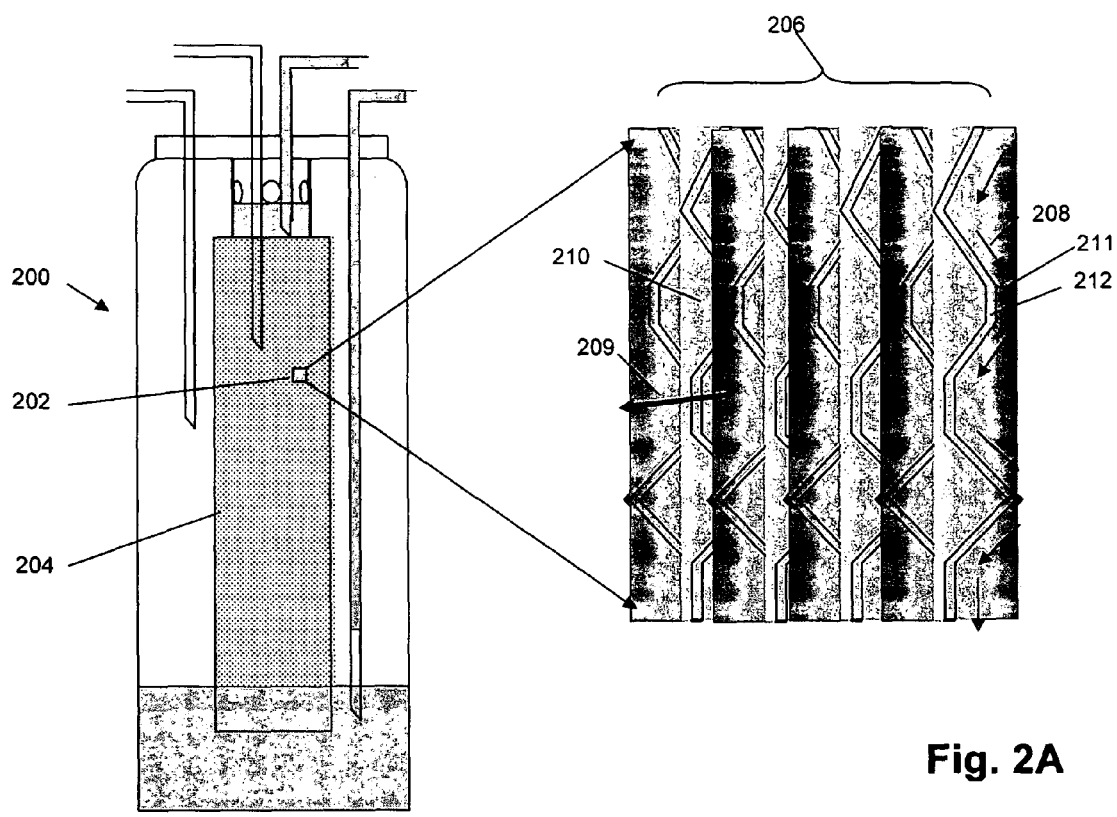
FIGS. 2A and 2B are side views illustrating culture medium flow over a support matrix of the cell culture bioreactor, constructed in accordance with the present invention, versus under a condition wherein support matrix pores are flooded.

FIG. 2A illustrates the structure of a support matrix material and how it interacts with a flow of culture medium in the device of this invention. The structure 206 is a blow-up of small section 202 of the support matrix 204 disposed in the culture chamber 200. As mentioned above, in one aspect, the support matrix 204 comprises a porous material having continuous open pores 210 that are formed from interlacing and interconnected fiber, or porous foam, which are illustrated in blow-up 206. Under desired operation, culture medium 211 flows 208 in a thin film over the surface of the fiber 212. A flow rate is selected so that the pores 210 are un-obstructed so that gas can freely flow 209 through the support matrix 204.

Figure 2B:
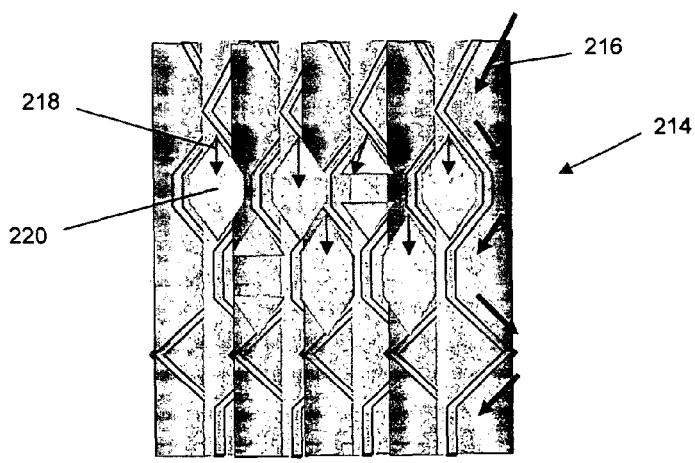

As illustrated in FIG. 2B, when a flow rate for the culture medium is too high 216, a volume of the culture medium flows through 218, and thereby floods multiple pores 220. Such flooding is undesirable as it interferes with the free access of local regions of support matrix 204 to air circulation. It may be noted here that in the currently used submerged sponge systems all of the pores are flooded which leads to a significantly less efficient gas, and nutrient exchange.

The following experiments demonstrates the efficiency of the present device over prior art methods for cell culture.

Figure 3:
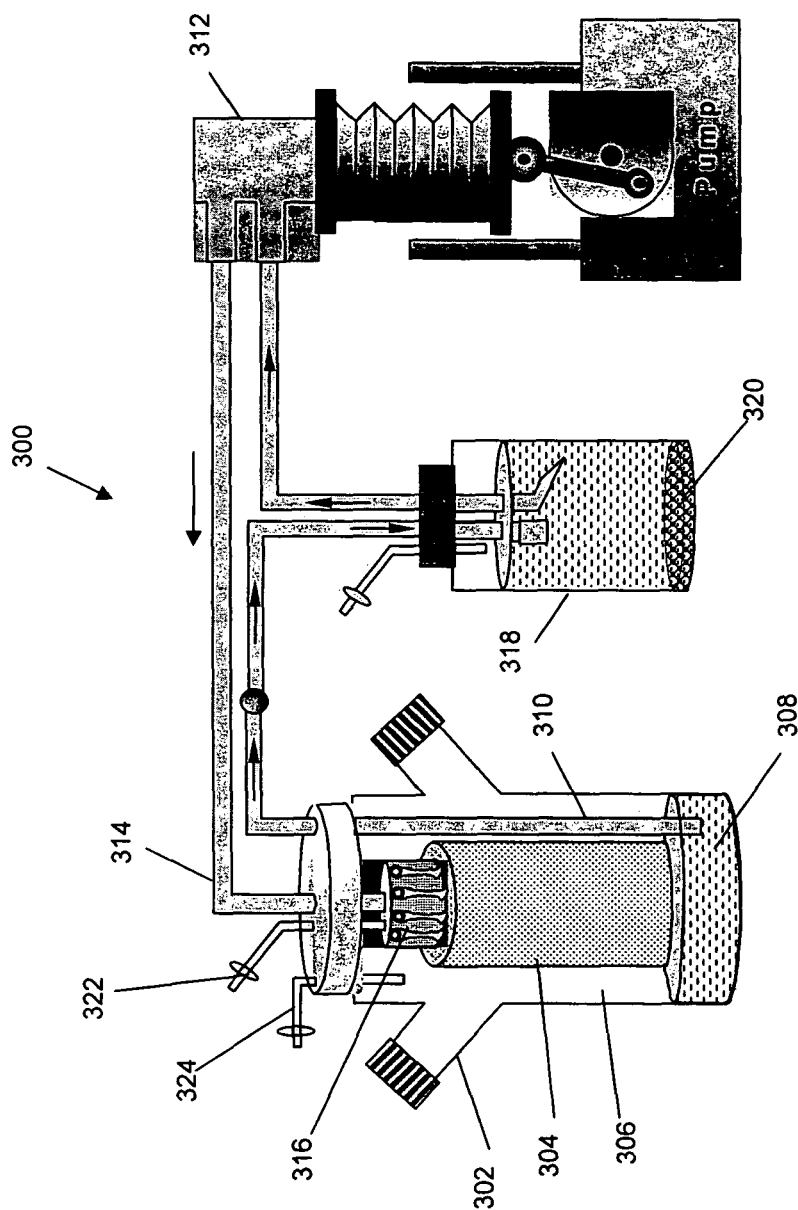
FIG. 3 is a perspective view illustrating a bioreactor system employing a culture chamber, constructed in accordance with the present invention.

In the first experiment, a one liter Bellco flask with 2 side arms was assembled as illustrated in FIGS. 1, 2 & 3. The sterilized bioreactor was populated with cells as follows: Five "T"-75 flasks containing a culture medium consisting of DMEM (Delbecco's Modified Eagle Media)+10% FBS (fetal bovine serum)+4 mM fresh glutamine were inoculated with a hybridoma cell line producing, monoclonal antibody and incubated in a 6% $CO_2$ 37° C. incubator until the cell count reached a concentration of $10^5$ viable cells/mL. The cells were then transferred into the washed and sterilized bioreactor. The bioreactor was incubated at 37° C. The medium circulation rate was set to about 35 ml/min. The air pump, which circulated the air with 6% $CO_2$, was adjusted to flow at approximately 3 bubbles per second. For the first 10 days 250 mL of the culture medium was exchanged daily. On day-11 the harvesting of the began.

In experiment two, two "T"-75 flasks were set up to allow growing to a confluence of approximately $5\times10^5$ cells/mL. The cells were then allowed to grow to the "death phase" which took about 3 weeks. The spent medium was frozen for later analysis and were used as control. Initially, 250 mls. Samples of spent medium was collected as harvest and frozen. Then 250 ml of fresh medium was used to replace the spent medium. On week four, the replacement volume was reduced to 50 mls/day. Cell viability was monitored daily by microscopic examination. Cell viability stabilized at approximately 80% throughout the remaining time. After six weeks the culturing was terminated as planned.

Results indicated that cells grew much more rapidly and to a higher cell density and thus, the end product, using the device and method of the present invention compared to prior art batch processing and submersion methods.

The present invention thus presents a novel device and method for efficient gas exchange supporting cell culture systems which provides a rapid continuous flowing thin film (and thus, high surface area) of nutrient containing, gassed, culture medium. Foam causing turbulence during rapid recycling of the culture medium is avoided by a novel recycling overflow/reservoir system. Such a system places recycling medium gently onto the porous support matrix. Internal leaking is avoided by the design of the system, allowing any overflow (i.e., when the recycling rate is greater than the absorbency of the support matrix.) to be kept within the recycling aseptic reservoir environment.

In addition, the present invention uses less pressure (thus less energy, less system stress, less complexity) than current gas permeable membrane methods (such as hollow fiber or spiral wound gas exchangers). Pressure driven gas exchange is avoided by substituting gravity and capillary forces to provide the large surface-area gas exchange process.

Furthermore, the present invention allows significantly more efficient gas exchange than mixing, shaking, rocking, or sparging, because of the significantly increased surface area. The device of the present invention is directly or linearly scalable such that gas exchange diffusion rates are maintained when scaling up from small units to large units. The scaling up is accomplished by maintaining the thickness and height of the support matrix and the corresponding size of the culture chamber, but expanding the width to a useful production size. Linear scalability reduces manufacturing development time, significantly reducing development costs and time-to-market.

The foregoing exemplary descriptions and the illustrative preferred embodiments of the present invention have been explained in the drawings and described in detail, with varying modifications and alternative embodiments being taught. While the preferred embodiments of the subject invention, as described herein, have been presented for purposes of illustration and description and for a better understanding of the invention. It is not intended to be exhaustive or to limit the invention to the precise form disclosed; and obviously many modifications and variations are possible in light of the above teaching. The particular embodiments were chosen and described in some detail to best explain the principles of the invention and its practical application to thereby enable others skilled in the relevant art to best utilize the invention in various embodiments and with various modification as are suited to the particular use contemplated. It is intended that the invention be defined by the claims appended hereto. Furthermore, the invention as disclosed herein, may be suitably practiced in the absence of the specific elements which are disclosed herein.

What is claimed is:

1. A cell culture bioreactor device comprising:
   a. a culture chamber;
   b. a support matrix for biological cell growth thereupon, the matrix having a top end and at least one bottom end and mounted within the culture chamber;
   c. an external culture medium reservoir operationally connected to the culture chamber;
   d. a manifold in fluid communication with the culture medium reservoir, the manifold configured for receiving and distributing a culture medium and supported within the culture chamber in a position directly above the top end of the support matrix:
   e. fluid circulation means for moving the culture medium from the culture medium reservoir through the manifold operably located above the top end of the support matrix in such a manner that the culture medium flows from the manifold as a thin film over substantially an entire surface of the support matrix that supports the biological cell growth and wherein the thin film of culture medium is sufficient to supply nutrients and is thin enough to allow oxygen from the air to permeate or otherwise reach, from any surface of the support matrix, all of the biological cells grown on the support matrix; and
   f. aerating means for introducing air into and removing air from the culture chamber.

2. The cell culture bioreactor device of claim 1, wherein the support matrix mounted within the culture chamber is in fluid communication with the manifold and wherein the support matrix comprises a porous material having continuous open pores that permit substantially free transport of the culture medium with said nutrients and said oxygen through the support matrix; and wherein at least a portion of at least one lower end of the support matrix contacts the culture medium at the bottom of the culture chamber, and wherein said culture medium flows from said manifold in the thin film over substantially the entire surface of said support matrix contacting said biological cells with said nutrients contained in said culture medium to the bottom of said chamber.

3. The cell culture bioreactor device of claim 2, wherein culture chamber comprises a support rod mounted therein and wherein the manifold comprises an elongated, tubular device having a plurality of apertures positioned directly over the support rod, the elongated tubular device receiving culture medium from the fluid circulation means and through the apertures distributing the culture medium in a substantially vertical direction to a middle portion of the support matrix.

4. The cell culture bioreactor device of claim 1, wherein the culture medium flows by gravity-assisted capillary, wicking through the support matrix.

5. The cell culture bioreactor device of claim 1, further comprising an elongated support rod mounted within the culture chamber and positioned directly below the manifold; wherein the support matrix is in the form of a sheet the matrix further containing a middle sheet portion between a first sheet end and a second sheet end, wherein the support matrix is mounted (i) by draping the matrix over the support rod thereby positioning the matrix to receive culture medium from the manifold onto the middle sheet portion and (ii) providing the culture medium to the bottom of the culture chamber and resting the first and second sheet ends in the culture medium at the bottom of the culture chamber.

6. The cell culture bioreactor device of claim 1, wherein the support matrix is substantially cylindrical-shaped, wherein the manifold has a receptacle portion mounted at a top end of the culture chamber, and wherein the top end of the support matrix is mounted to the manifold to receive culture medium from the manifold and wherein by providing the culture medium to the bottom of the culture chamber the bottom end of the support matrix is positioned to rest in the culture medium at a bottom end of the culture chamber.

7. The cell culture bioreactor device of claim 6, wherein the manifold is also cylindrical in shape, the cylindrical manifold receiving culture medium from the fluid circulation means and distributing the culture medium in a substantially horizontal direction by overflow of the culture medium around a receptacle portion of the manifold receiving the first cylinder end of the support matrix.

8. The cell culture bioreactor device of claim 7, wherein the support matrix divides the culture chamber into at least a first region and a second region, the aerating means comprising a gas inlet in communication with the first region and a gas outlet in communication with the second region, the gas inlet and gas outlet being operationally connected to a regulated atmospheric gas source for the culture chamber that provides a flow of an atmospheric gas from the gas inlet through the support matrix to the gas outlet.

9. The cell culture bioreactor device of claim 8 wherein the first region of the culture chamber has a first pressure and the second region of the culture chamber has a second pressure, and wherein the first pressure is substantially equivalent to the second pressure, and wherein in the device support of said biological cell growth comprises suspending the biological cells on the matrix, attaching the biological cells to the matrix, or a combination thereof.

10. The cell culture bioreactor device of claim 1 wherein the support matrix is an elastic porous material having continuous open pores formed of interlacing and interconnected fibers and having a hydrophilic surface suitable as a substrate for a biological cell, the continuous open pores of the support matrix providing substantially equivalent communication of any location on the surface of the support matrix with the interior of the culture chamber.

11. The cell culture bioreactor device of claim 10, wherein the thin film of the culture medium has a thickness less than approximately one millimeter, to provide for a simultaneous oxygenation and nutrition of the biological cells by dispersing the oxygen and the nutrients across the surface of the support matrix as well as through the porous support matrix.

12. The cell culture bioreactor device of claim 1, wherein the fluid circulation means has a fluid delivery rate for non-turbulently delivering the culture medium through the manifold to the support matrix in a non-turbulent and non-foam causing tribulation.

13. The cell culture bioreactor device of claim 12, wherein the fluid delivery rate of the fluid circulation means has a value such that flooding the support matrix with the culture medium produces substantially no back pressure in the culture chamber obstructing the flow of atmosphere; wherein biological cells are capable of growing on the support matrix, wherein the support matrix is a spongy, mesh material; and wherein the culture medium flows through the sides and the center of the support matrix thereby wicking and permeating the entire support matrix material with culture medium.

14. The cell culture bioreactor device of claim 1, further comprising:
regeneration means operationally associated with the fluid circulation means, the regeneration means (a) receiving the culture medium from an outlet, (b) optionally removing a waste material or extracting a material from the received culture medium, (c) optionally replenishing nutrients to the received, waste-removed, or extracted culture medium, and (d) delivering the received, waste-removed, extracted, or replenished culture medium to the fluid circulation means.

15. The cell culture bioreactor device of claim 1, wherein the external culture medium reservoir is positioned above the culture chamber, wherein the culture medium is provided through the support matrix to the bottom of the culture chamber and wherein at least a portion of the support matrix contacts the culture medium at the bottom end of the chamber.

* * * * *